(12) United States Patent
Benedek et al.

(10) Patent No.: US 8,114,358 B2
(45) Date of Patent: Feb. 14, 2012

(54) APPARATUS AND METHOD FOR TREATING IMPURITIES IN AIR AND MATERIALS

(75) Inventors: Karen Benedek, Winchester, MA (US); Philip C. Carbone, North Reading, MA (US)

(73) Assignee: Primaira, LLC, Woburn, MA (US)

( * ) Notice: Subject to any disclaimer, the term of this patent is extended or adjusted under 35 U.S.C. 154(b) by 54 days.

(21) Appl. No.: 12/312,690

(22) PCT Filed: Nov. 21, 2007

(86) PCT No.: PCT/US2007/024347
§ 371 (c)(1),
(2), (4) Date: May 21, 2009

(87) PCT Pub. No.: WO2008/127315
PCT Pub. Date: Oct. 23, 2008

(65) Prior Publication Data
US 2010/0054989 A1    Mar. 4, 2010

(51) Int. Cl.
*A61L 9/00*     (2006.01)
*A61L 2/00*     (2006.01)
*A62B 7/08*     (2006.01)
*B01J 19/08*    (2006.01)
*B03C 3/00*     (2006.01)
*B01D 47/02*    (2006.01)
*B01D 39/00*    (2006.01)

(52) U.S. Cl. ............... 422/305; 422/1; 422/3; 422/5; 422/22; 422/24; 422/121; 422/123; 422/186.07; 422/306; 95/57; 95/226; 96/224

(58) Field of Classification Search .............. 422/1, 3, 422/5, 22, 24, 121, 123, 186.07, 306; 95/57, 95/226; 96/224
See application file for complete search history.

(56) References Cited

U.S. PATENT DOCUMENTS

| 4,904,289 | A | 2/1990 | Miyakami et al. |
| 4,990,311 | A | 2/1991 | Hirai et al. |
| 5,015,442 | A | 5/1991 | Hirai |
| 5,152,077 | A | 10/1992 | Liang |

(Continued)

FOREIGN PATENT DOCUMENTS

DE    36 37 702 A1    5/1988

(Continued)

OTHER PUBLICATIONS

Co-Pending U.S. Appl. No. 12/587,948, filed Oct. 14, 2009; inventors Karen Benedek et al.; title Apparatus and Method for Treating Impurities in Air and Materials.

*Primary Examiner* — Jill Warden
*Assistant Examiner* — Monzer Chorbaji
(74) *Attorney, Agent, or Firm* — Pauley Petersen & Erickson

(57) ABSTRACT

An apparatus and method for sanitizing, decontaminating, deodorizing, conditioning, drying, treating, cleaning, modifying and/or otherwise improving an atmosphere within a container. The container can be a bag or other housing for equipment, food and/or suitable material. Ozone is generated within an atmosphere that is exposed to the materials. The generated ozone is mixed with the atmosphere. At least a portion of the generated ozone is then removed from the mixed atmosphere. The apparatus and method of this invention can be used to treat contaminated sports equipment and the like, as well as to treat food storage atmospheres, such as those exposed to fresh fruits and vegetables.

13 Claims, 15 Drawing Sheets

U.S. PATENT DOCUMENTS

| | | |
|---|---|---|
| 5,230,220 A | 7/1993 | Kang et al. |
| 5,369,892 A | 12/1994 | Dhaemers |
| 6,134,806 A * | 10/2000 | Dhaemers ................ 34/404 |
| 6,391,272 B1 * | 5/2002 | Schroeder ............ 423/245.3 |
| 6,845,569 B1 | 1/2005 | Kim |
| 2002/0139124 A1 | 10/2002 | Palermo |
| 2004/0003511 A1 | 1/2004 | Silver |
| 2004/0146437 A1 | 7/2004 | Arts et al. |
| 2004/0161371 A1 | 8/2004 | Russell et al. |
| 2005/0089458 A1 | 4/2005 | Oke |
| 2006/0104858 A1 | 5/2006 | Potember et al. |
| 2008/0118395 A1 | 5/2008 | Benedek |

FOREIGN PATENT DOCUMENTS

| | | |
|---|---|---|
| EP | 0 269 941 A | 6/1988 |
| JP | 2002-263181 A | 9/2002 |
| JP | 2005-226861 A | 8/2005 |
| WO | WO 90/02572 A1 | 3/1990 |
| WO | WO 03/080375 A1 | 10/2003 |
| WO | WO 2008/103719 A1 | 8/2008 |
| WO | WO 2008/127315 A2 | 10/2008 |

* cited by examiner

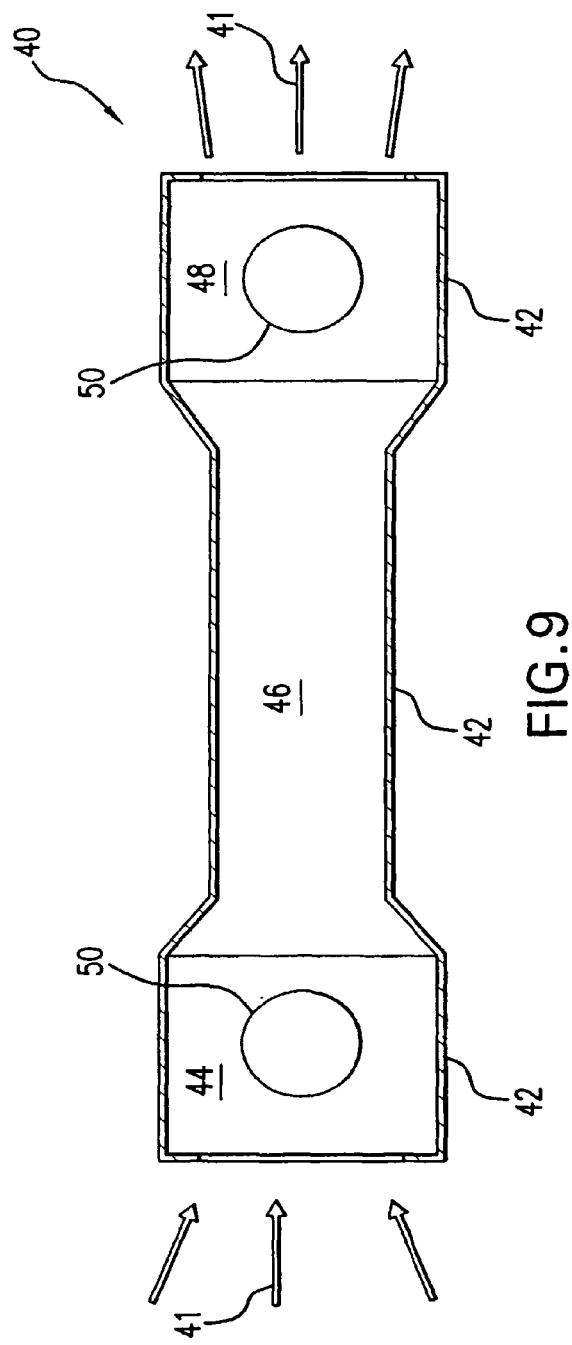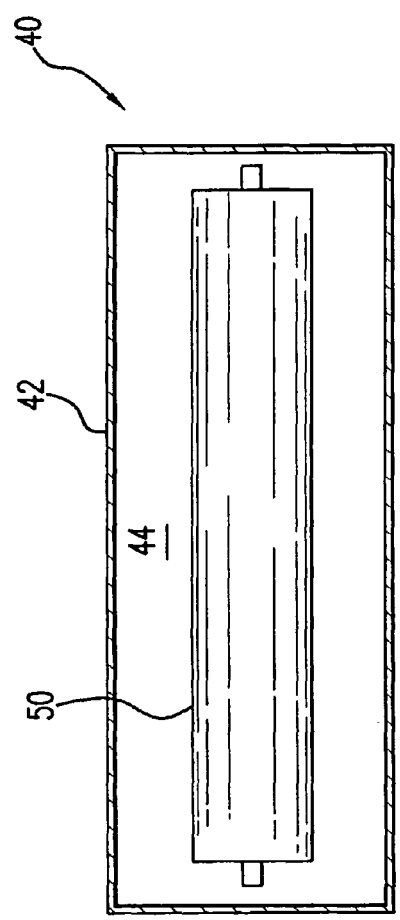

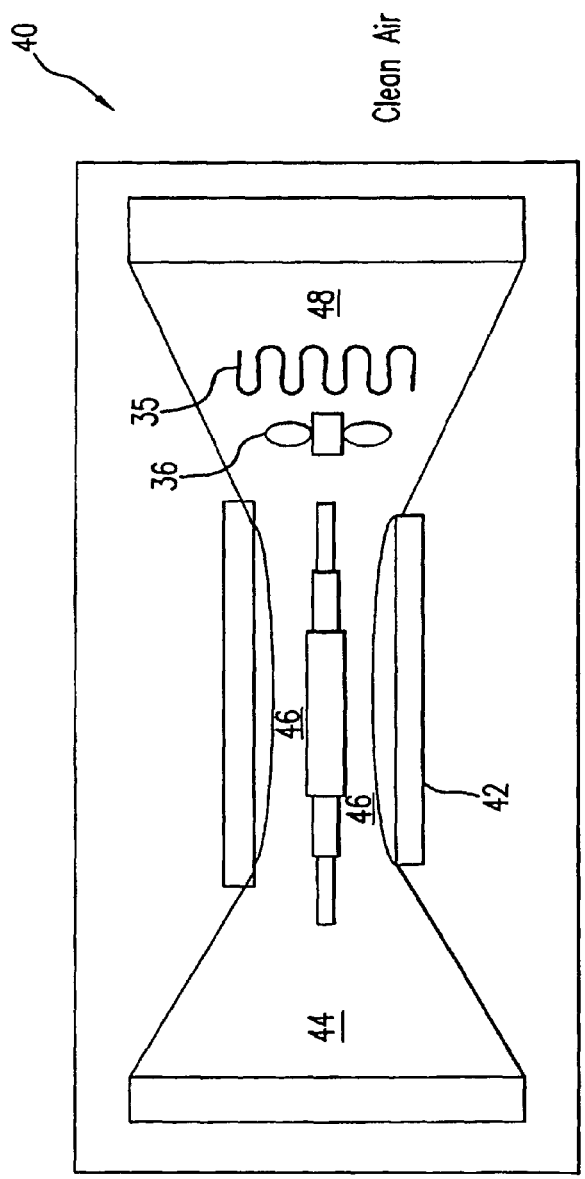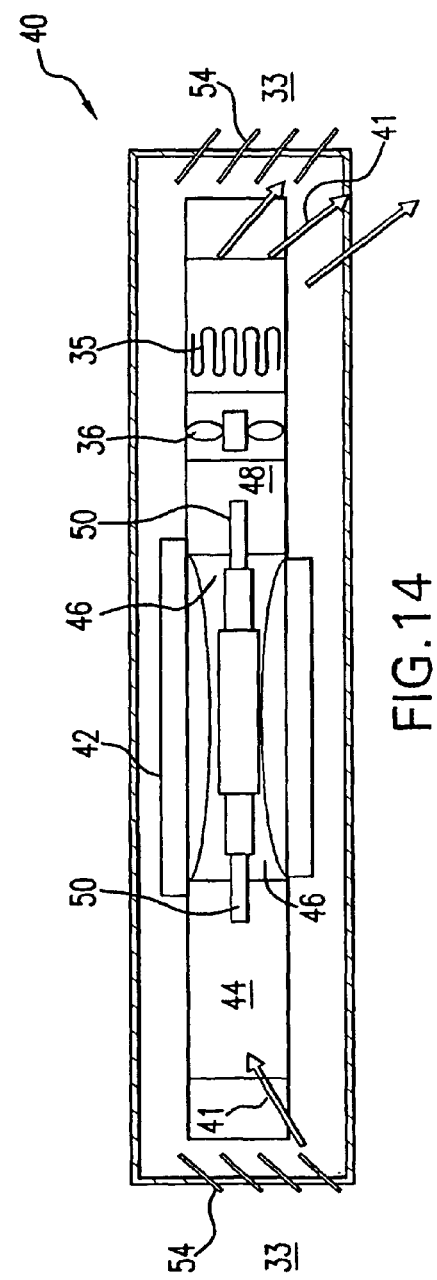
FIG. 13
FIG. 14

| Lamp Catalog Number | | Nominal Lamp Length | Lamp Watts | Approximate Lamp Current mA | Ultraviolet Output | | Ozone Output | Rated Effective Life (hrs) |
|---|---|---|---|---|---|---|---|---|
| Ozone Free | Ozone Producing | | | | Total Watts | Microwatts @ 1 meter | | |
| G18T6L/U | G18T6VH/U | 8-1/4" | 17 | 425 | 5.8 | 59 | 1.6 | 10.000 |
| G24T6L/U | G24T6VH/U | 11-1/4" | 25 | 425 | 8.5 | 82 | 2.3 | 10.000 |
| G30T6L/U | G30T6VH/U | 14-1/4" | 32 | 425 | 11.2 | 101 | 3.0 | 10.000 |
| G36T6L/U | G36T6VH/U | 17-1/4" | 39 | 425 | 13.8 | 120 | 3.7 | 10.000 |
| G48T6L/U | G48T6VH/U | 23-1/4" | 50 | 425 | 19.3 | 164 | 5.2 | 10.000 |

FIG.15

| Common Name | Ethylene Production | Ethylene Sensitivity |
|---|---|---|
| Apple | Very High (>100µl/kg-hr) | Highly Sensitive |
| Banana | Moderate (1-10µl/kg-hr) | Highly Sensitive |
| Broccoli | Very Low (<0.1µl/kg-hr) | Highly Sensitive |
| Citrus (oranges) | Very Low (<0.1µl/kg-hr) | Moderately Sensitive |
| Pears | High (10-100µl/kg-hr) | Highly Sensitive |
| Tomatoes (ripe) | Very Low (<0.1µl/kg-hr) | Highly Sensitive |
| Tomatoes (unripe) | High (10-100µl/kg-hr) | Low Sensitive |

FIG.16

| Known Ethylene Control Technology | Limitation for Transport and Storage Applications |
|---|---|
| Ventilation | Refrigerated shipping containers and storage facilities or devices are not designed for significant ventilation due to energy requirements to condition outside air, risk of contamination, risk of drying-out the fruit and vegetables, and difficulty ventilating individual cartons of fresh fruit and vegetables (FF&V) |
| Potassium Permanginate ($KMnO_4$) (absorption/catalytic oxidation of $C_2H_4$ to $H_2O$ and $CO_2$) | One-time use, this produce poses an environmental and cost burden due to the need to dispose of the $KMnO_4$ as a hazardous waste |
| Bromated Carbon (absorbent) | Costly and waste products must be disposed |
| Catalytic Oxidizers (e.g. $TiO_2$ photocatalytic oxidation, $C_2H_4$ to $H_2O$ and $CO_2$) | High pressure drop of catalytic reactor leads to excessive power requirement for air-flow through the reactor, it is difficult to draw the air out of individual FF&V shipping cartons to be cleaned, and long residence times required for significant ethylene reduction effectiveness results in an excessively large system. |

FIG. 17

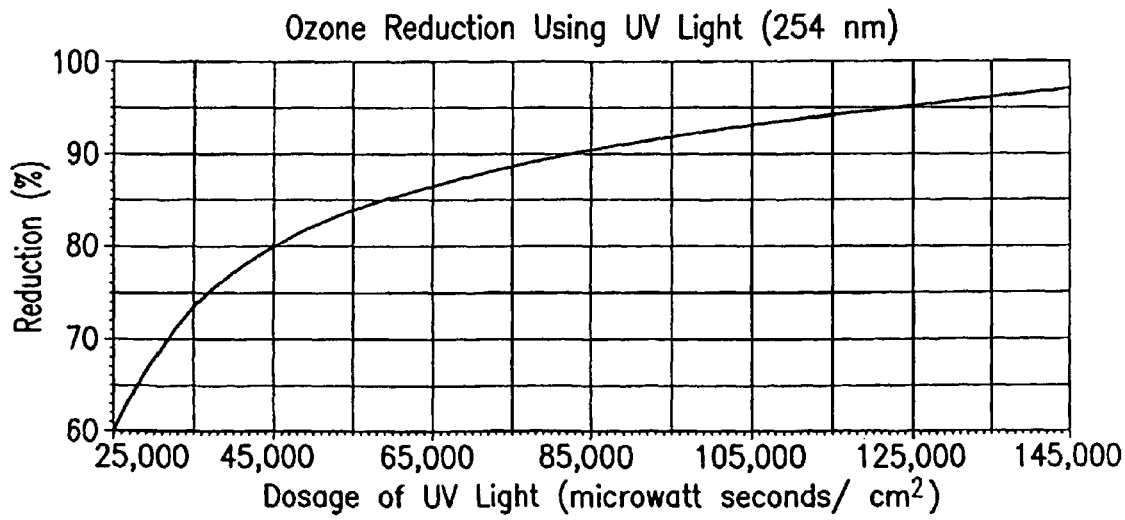

FIG. 18

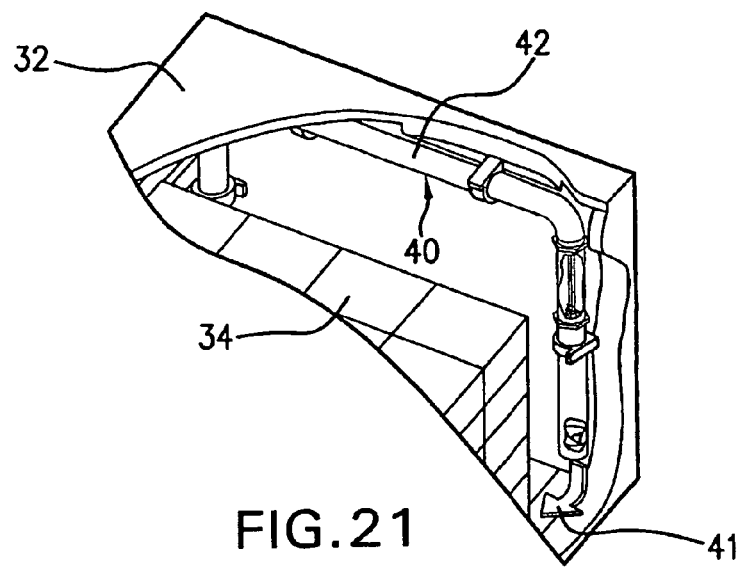
FIG.21
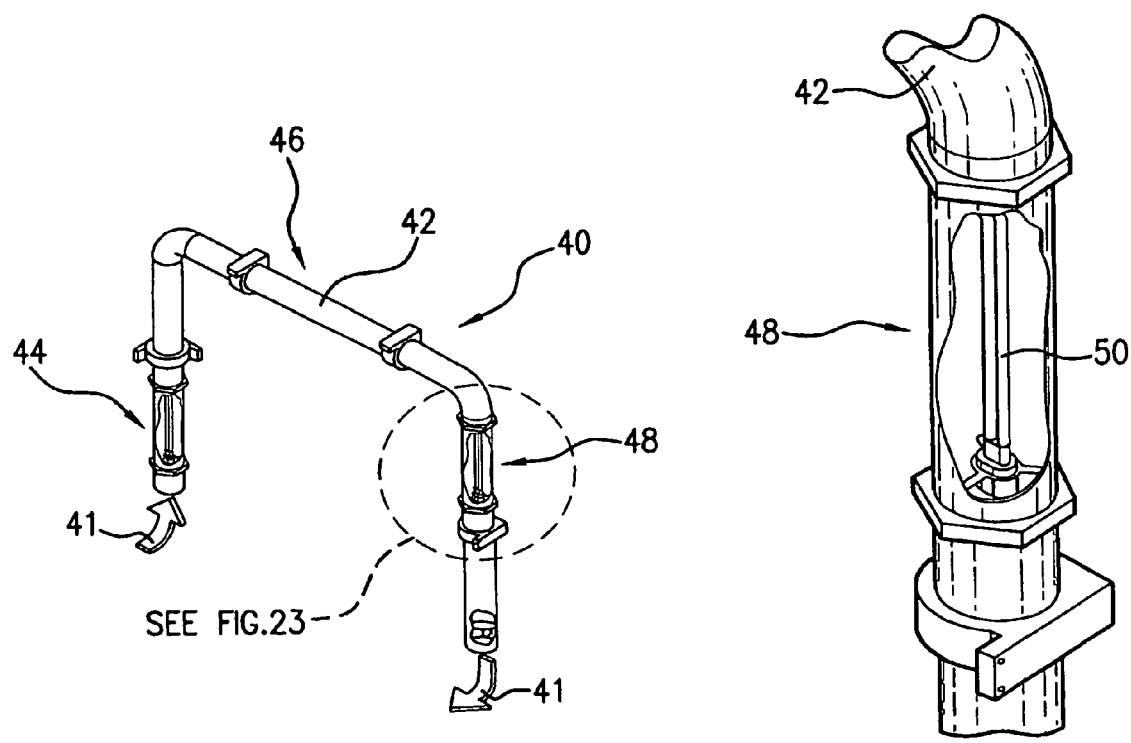
FIG.22
FIG.23

APPARATUS AND METHOD FOR TREATING IMPURITIES IN AIR AND MATERIALS

GOVERNMENT INTEREST

This invention was made with government support under DOD Contract Number W911QY-07-C-0005. The United States Government has certain rights in the invention as provided in the contract.

BACKGROUND OF THE INVENTION

1. Field of the Invention

This invention relates to a material and/or air cleaning apparatus and a method for removing impurities from the air, resulting in air that has been deodorized, dried, sanitized, treated, modified, improved and/or otherwise cleaned of undesired contaminants. More specifically, this invention relates to an apparatus and a method that uses UV light to generate ozone, uses the ozone to destroy impurities in the air, and then uses UV light to destroy ozone so that damaging ozone does not contact the sensitive materials or surfaces being cleaned.

2. Discussion of Related Art

A wide range of sports equipment is designed and used to protect the human body from injury. Equipment pieces are relatively large, bulky, oddly shaped, fitted with straps, and difficult to wash and dry. In soccer, a player wears shin guards and ankle guards to protect the lower leg. In hockey, a player wears knee pads, a chest protector, elbow pads, gloves, a helmet and hockey pants. In football, a player wears shoulder pads, leg and hip pads, a helmet, a neck roll, elbow pads and gloves. Bicyclists and roller blade skaters use helmets. Many sports require general or specialized footwear, such as cleats, sneakers, spikes, skates, roller blades and the like. Workers can wear similar equipment.

Protective equipment can be worn with direct contact against a skin or a head surface. Whether the equipment directly contacts the human body or is separated by clothing or a piece of cloth, sweat soaks into materials, such as pads, elastic material, straps, foam, and other materials. If not properly dried or cleaned, the sweat-soaked equipment becomes a site for growth of bacteria, mold, mildew, fungus, and other microorganisms that can spread disease, cause odor and/or damage or discolor the equipment. The equipment and the bag, bin or other storage container can become malodorous. Odors from the equipment can emanate from or through the container and make unpleasant the corresponding room, such as a vehicle compartment. Merely blowing air across the equipment to dry the equipment can more broadly release odors from the evaporated sweat and moisture into the room, house or other compartment. It is desirable to have an apparatus and/or method for drying, deodorizing, and/or sanitizing equipment, quickly and conveniently.

Known products in the marketplace have addressed this need. Dhaemers, U.S. Pat. No. 6,134,806 describes a portable sport equipment bag having an air distributor connected with a hose to a blower and an ozone generator operable to move pressurized air and ozone into the air distributor. The air distributor moves the air and ozone into the bag to dry the sports equipment contained within the bag, to destroy bacteria, molds and fungus in the bag. The ozone directly contacts the sports equipment, which can be a serious problem because ozone can destroy many equipment materials, such as when the ozone exists in air at concentrations that are high enough to kill undesirable microorganisms. When well mixed with contaminated air, ozone can more effectively and efficiently oxidize contaminants. Also, ozone is a lung irritant and can leak out of the equipment bag and dangerously be inhaled, such as when the user opens the sports equipment bag. These safety issues can be serious enough to warrant alternative approaches.

Dhaemers, U.S. Pat. No. 5,369,892 describes a dryer in the form of an armoire with an internal drying chamber for housing articles that are subjected to heated circulating air, to remove moisture from the articles. Ultraviolet lamps within the drying chamber destroy contaminants in the air and on the air conditioning coils, in the drying chamber. A similar configuration is taught by Liang, U.S. Pat. No. 5,152,077, which is limited because contaminated materials must be in a direct line of sight of a UV light source, in order to be sanitized. The clothes alone can restrict exposure between the material and the UV light. Air that circulates in the armoire cannot be deodorized.

There is a need for a convenient, efficient, cost effective and efficient method and apparatus for drying, deodorizing and/or sanitizing air and equipment, particularly without damaging the equipment.

Many other types of products can benefit from being dried, sanitized and deodorized, such as toys used at home or in commercial or institutional settings, including health care facilities, day care centers and/or schools. The materials used in toys and stuffed animals makes it difficult to clean them quickly and conveniently. Many toys need to be individually wiped with disinfectant to clean their surfaces. Disinfectants and wipes can be used to clean toys. These cleaning procedures are time consuming and burdensome.

There is a need for a method and apparatus for drying, deodorizing, and/or sanitizing a variety of products, quickly, safely and/or effectively, with minimal physical or chemical impact to the products.

Ethylene gas ($C_2H_4$) accumulates during the transport and storage of fresh fruits and vegetables and thus causes a problem for commercial agriculture and consumers. Small amounts of ethylene, sometimes less than 1 ppm, can induce fruit ripening, and can produce undesirable flavors such as bitterness, colors, such as yellowing or browning, and textures, such as softening, and thus can increase susceptibility to disease. Certain fruits and vegetables naturally generate ethylene during a ripening cycle. Other fruits and vegetables are highly sensitive to the presence of ethylene, but may or may not actually produce ethylene. The table in FIG. 16 lists some fruits and vegetables and known ethylene production rates and sensitivities.

The amount of ethylene that produces undesirable amounts or characteristics varies with different fruits and vegetables, but ethylene concentrations in the range of 0.1-10 ppm can produce a significant effect. There is a need for a system that removes ethylene from the air within a fruit or vegetable storage container while not damaging the fruits or vegetables.

Because there is significant industry value in maintaining fresh fruits and vegetables during transportation and storage, some technologies have been researched, developed and commercialized to control ethylene. These conventional methods and their limitations are shown in the table of FIG. 17.

There is a need for an alternative approach to ethylene control that would be less expensive, consume less power, and require less space.

SUMMARY OF THE INVENTION

It is one object of this invention to provide an apparatus and method for oxidizing the ethylene to carbon dioxide and water using UV-generated ozone.

It is another object of this invention to produce ozone to destroy ethylene and then to dissociate the excess ozone back to oxygen, to maintain acceptable levels of ozone within a shipping or storage container, for example that carries fresh fruits and vegetables.

According to this invention, ethylene can be oxidized in an ethylene control unit and/or in ambient air of the storage container, such as at a lower ozone concentration. This dual approach can maximize ethylene removal from the container air and/or the produce packages. This dual approach can also minimize negative effects of ozone concentrations in an air handling system or in the produce itself. UV-generated ozone can also be used to remove additional pathogens that can degrade produce quality, such as with certain fungus or mold spores. The apparatus and method of this invention can meet application requirements of a wide range of container sizes and refrigeration or other environmental control systems.

The method and system of this invention can generate, use, and destroy ozone, for example to remove ethylene and/or other impurities in the air or atmosphere within fresh fruit and vegetable containers. In one embodiment of this invention, ozone is both generated and destroyed by UV light rays. The ethylene removal apparatus and/or method can be accomplished with a wide variety of known configurations of storage containers, air flow patterns and/or refrigeration units.

According to this invention, it is possible to dry, deodorize and sanitize materials and their surrounding air. The materials can be sports equipment stored in a sports bag or an equipment bin, toys stored in a toy box and/or fruits or vegetables stored in a refrigerator or produce storage container.

According to this invention, it is possible to clean, deodorize, and sanitize materials by circulating cleaned and conditioned air across the materials. The contaminants that are transferred from the materials to the air are treated in an air cleaning unit. The cleaned air is circulated back across the materials, such as in a convective manner. Air flow and/or heat can be used to drive the contaminants from the materials into the air. The contaminants can be, for example, moisture, volatile matter, such as odors, bacteria, spores, dirt, or other gases, liquids and/or microorganisms.

The contaminants that are driven into an air stream can be drawn into a compact, low-cost, effective cleaning unit where the contaminants are destroyed. The cleaned air can be re-circulated back to the storage container.

This invention provides a method and device to generate, use, and ultimately at least partially destroy the generated ozone for decontamination, deodorization, and/or conditioning of the air and/or the materials. The air cleaning unit can be positioned inside a chamber of various suitable configurations or designs. Air that requires cleaning and deodorization is drawn from the chamber into the cleaning unit, passes across an ozone generator, such as a UV bulb that emits light rays in the UV wavelength that generates ozone. The ozone-laden, contaminated air can be further drawn through a mixing zone to establish enhanced contact between the generated ozone and the contaminants. The clean air is then drawn across a second UV bulb that emits in the UV wavelength that destroys ozone. Clean, ozone-free air is then reintroduced to the storage chamber.

One or more additional treatment devices may be placed in the chamber to heat, dry, cool or dilute the air stream that circulates through the air cleaning unit.

The system of this invention, which includes the apparatus and/or the method, can produce ozone to destroy contaminants and then used to dissociate the excess ozone back to oxygen in order to maintain appropriate levels of ozone within the storage container. The system of this invention provides a number of significant benefits compared to existing technology.

Circulation of air and ozone through a well designed mixing unit can be more efficient at cleaning the air than by injecting gaseous ozone, at non-hazardous levels, into still or calm air or other ambient conditions. It appears that at low concentrations of ozone, random encounters with contaminants is too slow of a process. However, there can be significant benefits to combining both of these methods to maximize benefits from ozone use.

This invention provides two opportunities to oxidize the odors and the microorganisms, one in an air cleaning unit, and the second, such as at a lower ozone concentration, in the ambient air of the storage container. This dual approach can better remove impurities from the air in the storage container and from surfaces of the materials. Ozone concentrations are relatively high in the air cleaning unit and the mixing rates between the ozone and the air is relatively high, and thus the oxidation rates of the impurities is relatively high. The air in the storage container can be quickly deodorized and sanitized. The concentration of ozone at the exit of the air cleaning unit can be precisely established. A very low concentration of ozone can be established in the storage container in order to sanitize surfaces of the materials, such as over a longer period of time. This dual approach can minimize negative effects of ozone concentrations in the air handling system or the surface of the sports or other equipment.

BRIEF DESCRIPTION OF THE DRAWINGS

The above and other features and objects of this invention are better understood from the following detailed description taken in view of the drawings wherein:

FIG. 9 is a diagrammatic perspective view showing a section of the air cleaner unit, as shown in FIG. 8;

FIG. 10 is a diagrammatic sectional side view of the air cleaner unit, as shown in FIG. 8;

FIG. 13 is a schematic top view of the air cleaner unit, as shown in FIG. 12;

FIG. 14 is a schematic side view of the air cleaner unit, as shown in FIG. 12;

FIG. 15 is table showing ozone-generating ultraviolet light performance parameters;

FIG. 16 is a table showing ethylene production and sensitivity of selected produce;

FIG. 17 is a table showing conventional ethylene control technologies and corresponding limitations; and FIG. 18 is a graph showing a reduction of ozone using ultraviolet light, according to one embodiment of this invention;

FIG. 21 is a partial cut-away perspective view of an air cleaning unit mounted within a container, according to another embodiment of this invention;

FIG. 22 is a partial cut-away perspective view of an air cleaning unit, according to the embodiment shown in FIG. 21; and FIG. 23 is an exploded partial cut-away perspective view of an ozone removal section, according to one embodiment of this invention.

DESCRIPTION OF PREFERRED EMBODIMENTS

Throughout this specification and in the claims, the term air cleaning unit is intended to relate to an apparatus for sanitizing, decontaminating, deodorizing, conditioning, drying and/or otherwise treating, cleaning, modifying and/or improving an atmosphere within a container.

Figure 1:
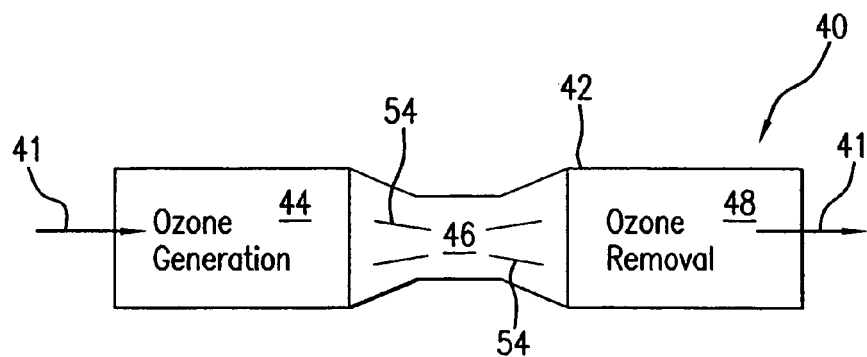
FIG. 1 is a diagrammatic view showing three elements of an air cleaner, including an ozone generation zone, a mixing zone and an ozone dissociation zone, according to one embodiment of this invention.
Figure 2:
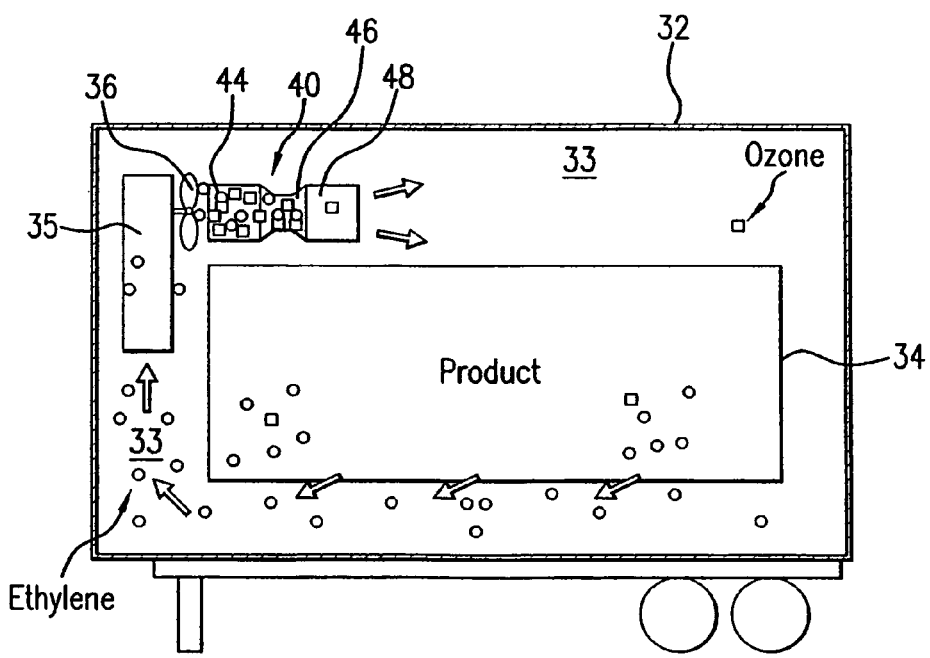
FIG. 2 is a diagrammatic showing an inside of a container, such as a refrigerated truck trailer, a housing and an evaporator, an air cleaner, and a material or product, according to one embodiment of this invention.
Figure 3:
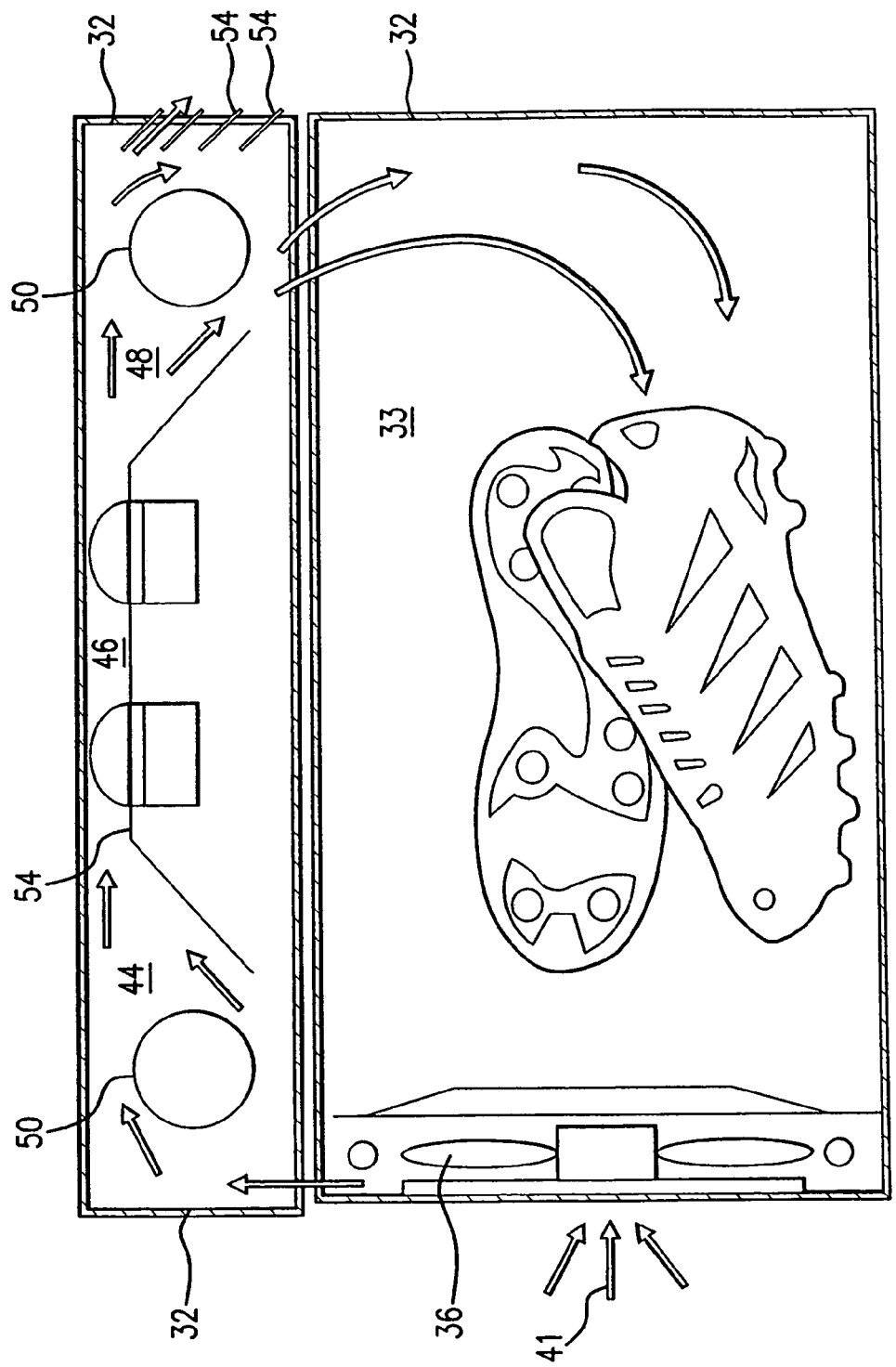
FIG. 3 is a diagrammatic side view of a cylindrical configuration of an air cleaner unit, according to one embodiment of this invention.
Figure 4:
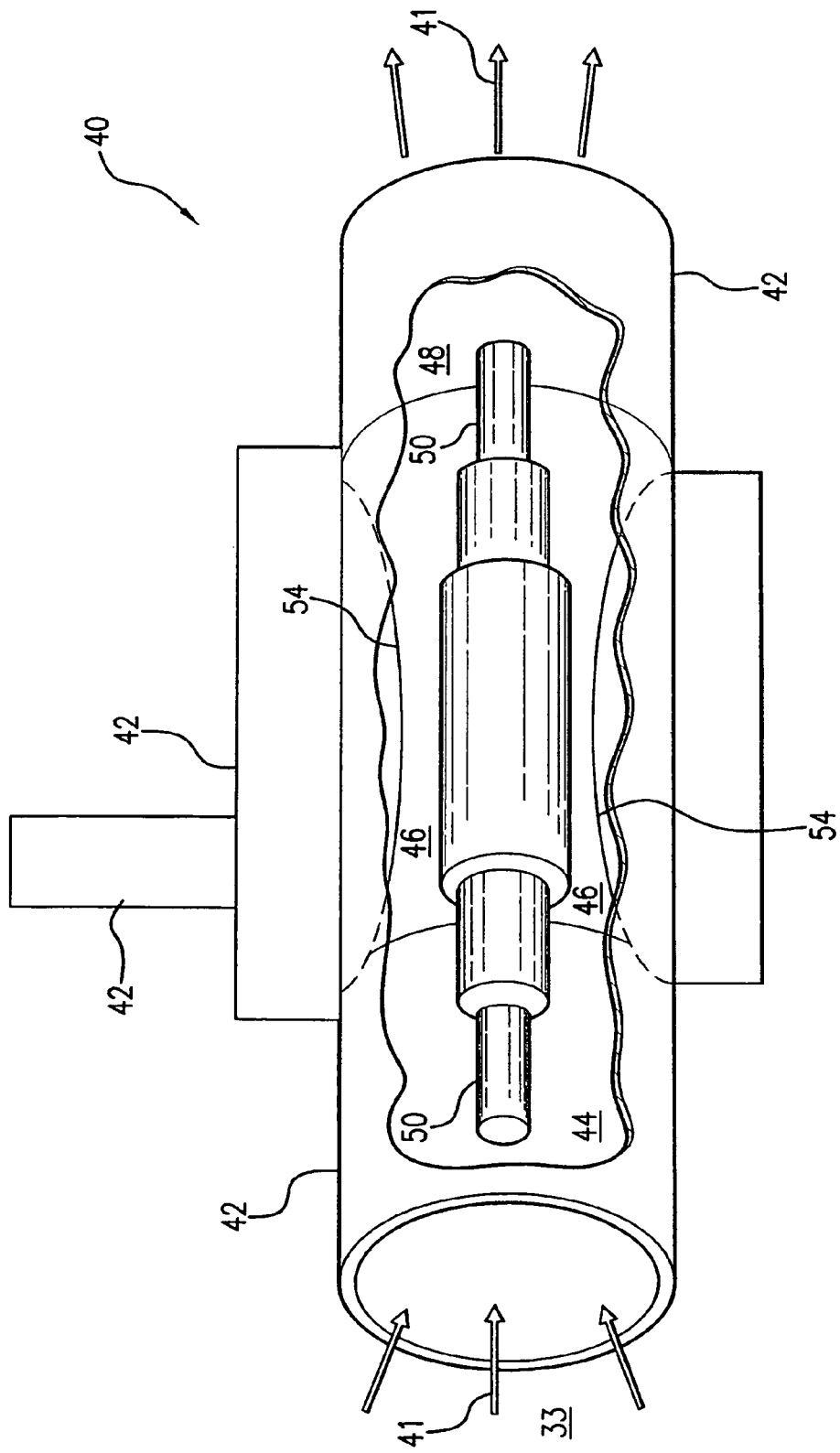
FIG. 4 is a diagrammatic partial sectional view of an air cleaner unit, according to one embodiment of this invention.
Figure 5:
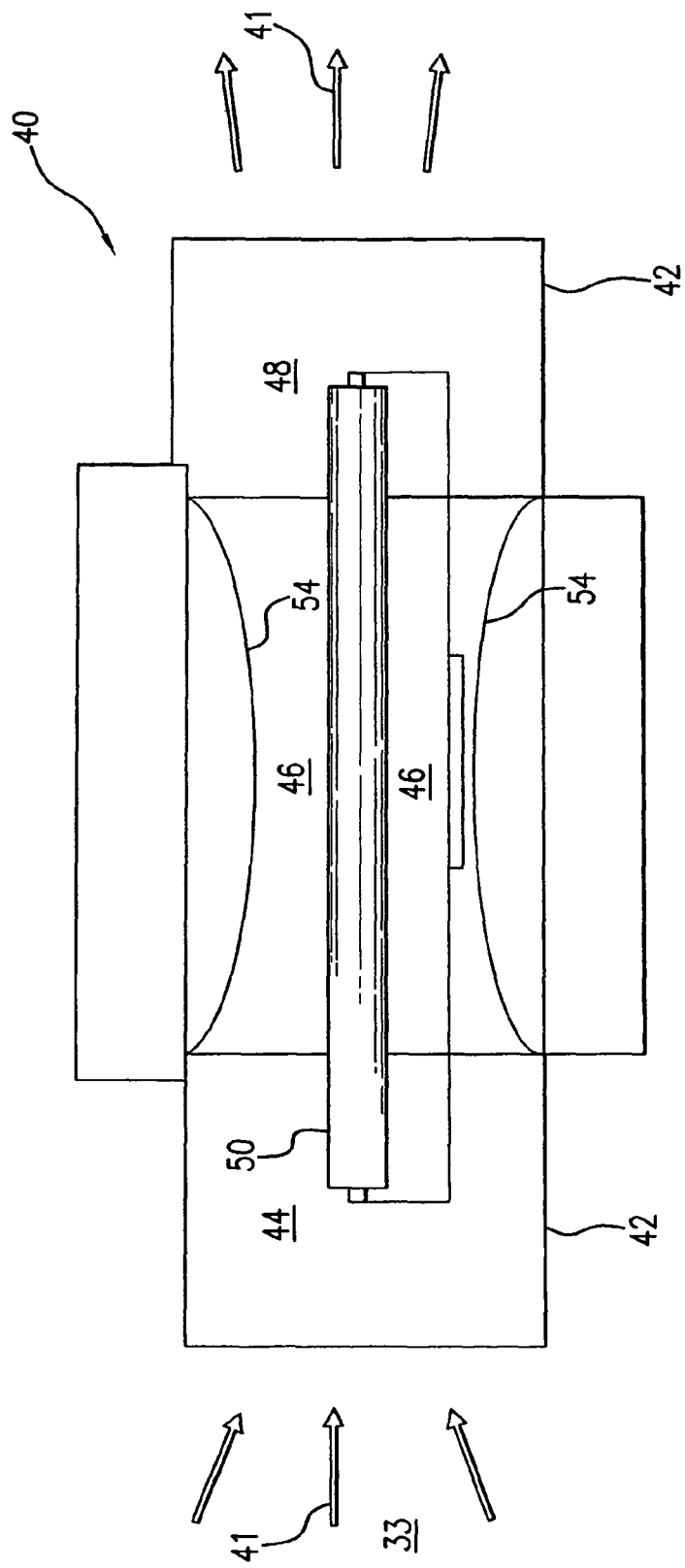
FIG. 5 is a diagrammatic partial sectional view of an air cleaner unit, according to another embodiment of this invention.
Figure 6:
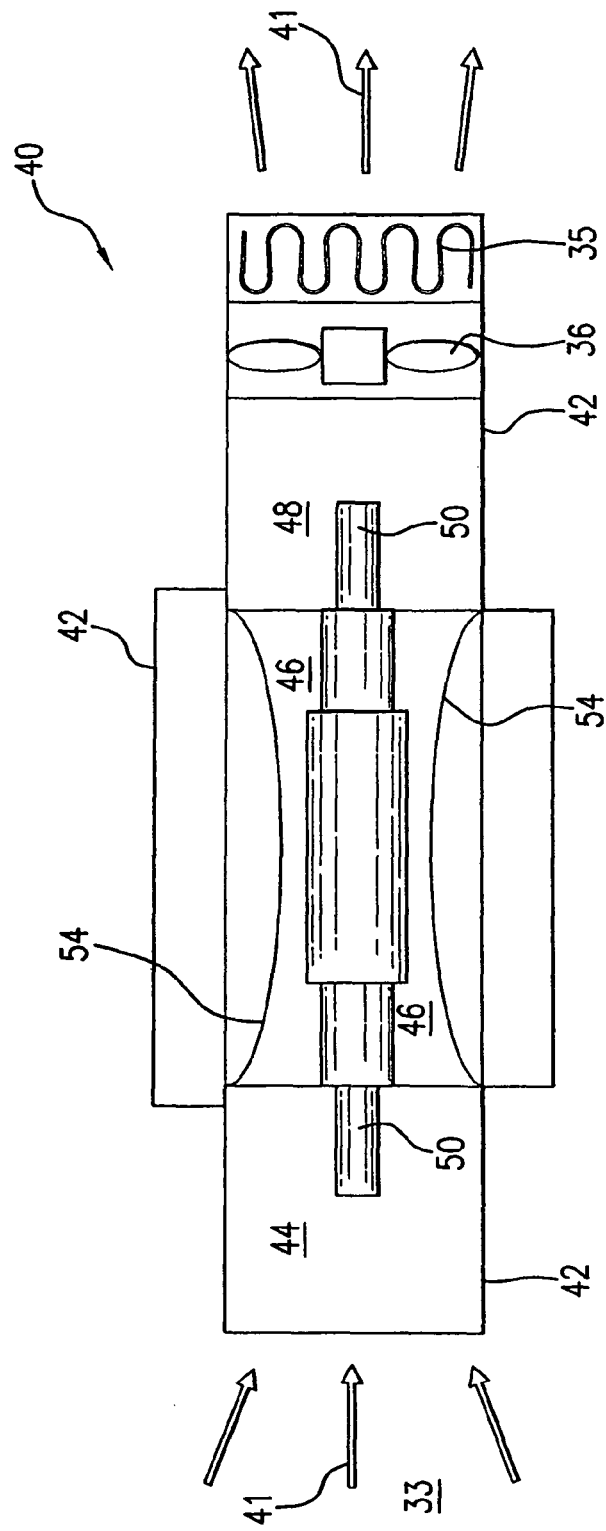
FIG. 6 is a diagrammatic partial sectional view of an air cleaner unit, according to one embodiment of this invention.
Figure 7:
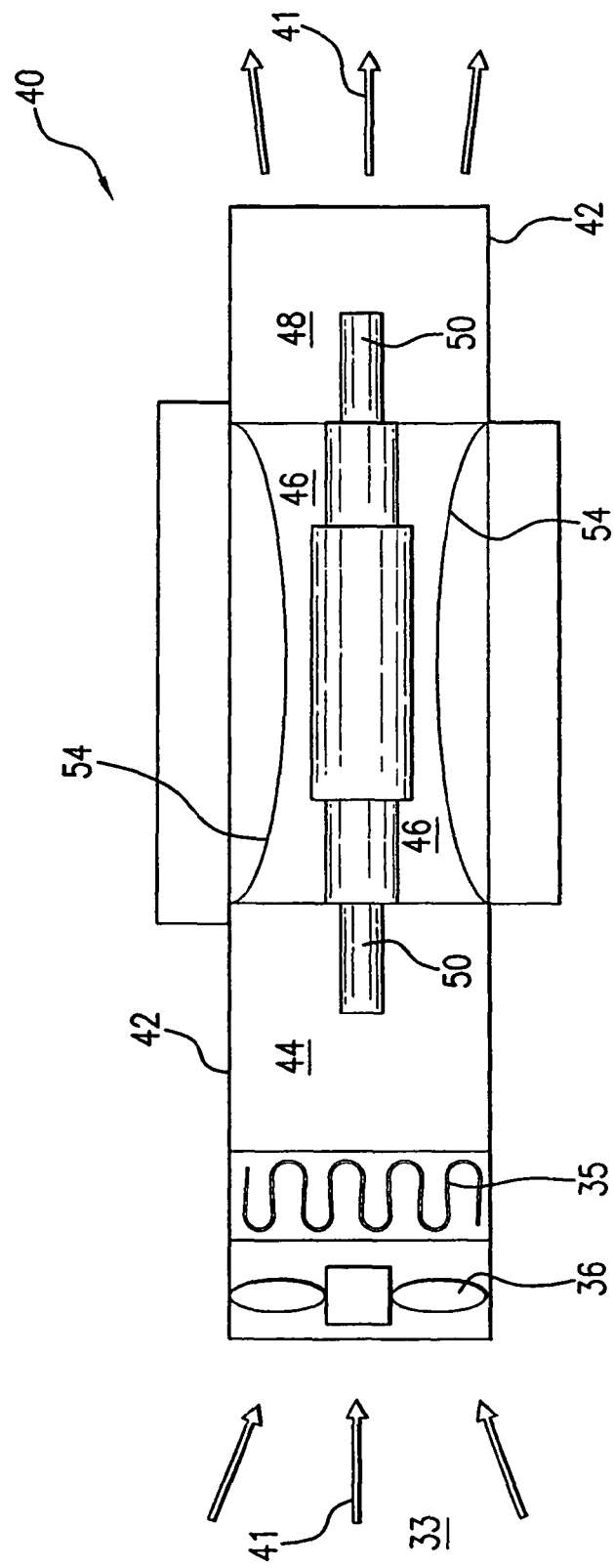
FIG. 7 is a diagrammatic partial section view of an air cleaner unit, according to one embodiment of this invention.
Figure 8:
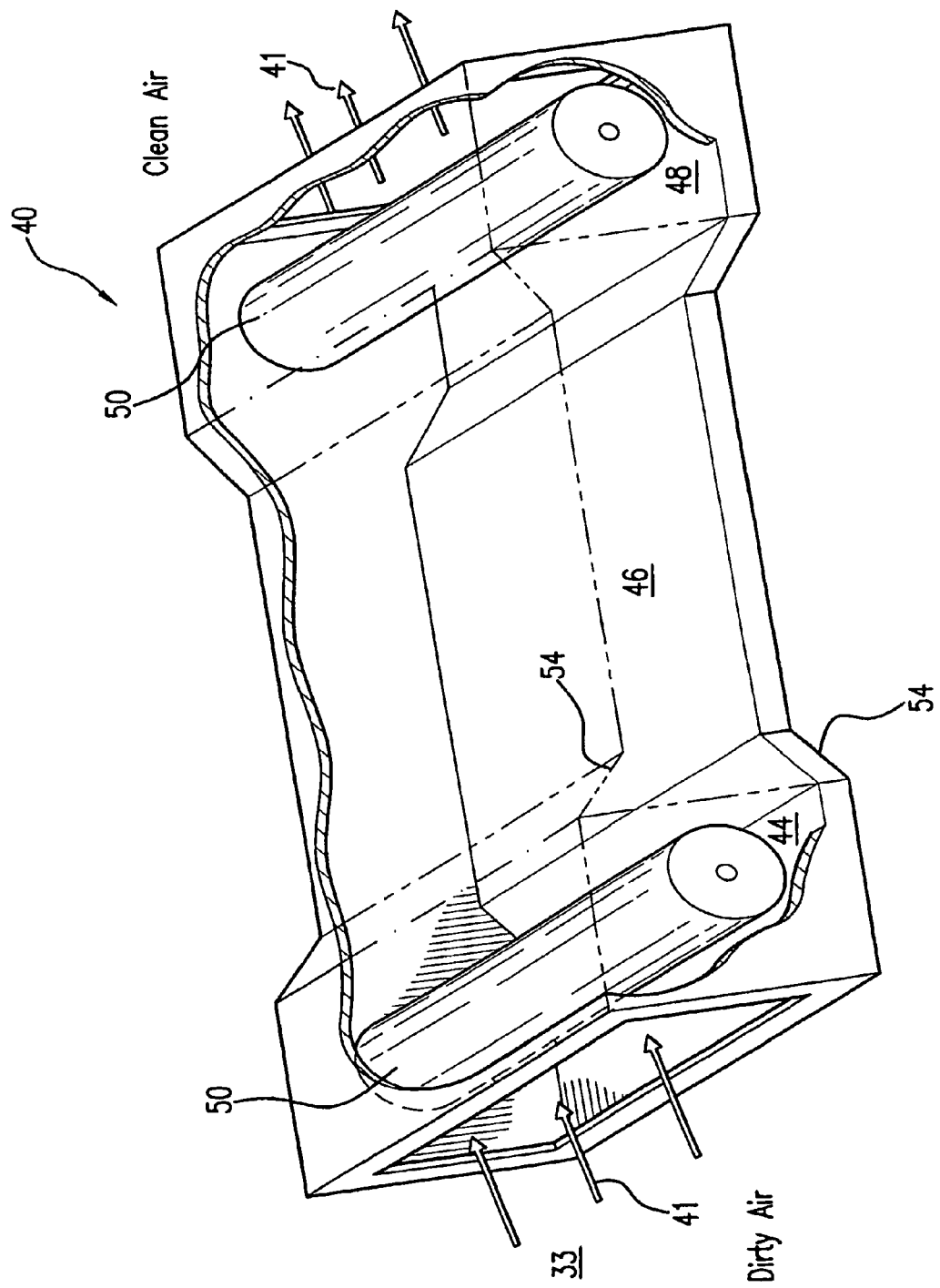
FIG. 8 is a diagrammatic perspective view of an air cleaner unit, according to one embodiment of this invention.
Figure 11:
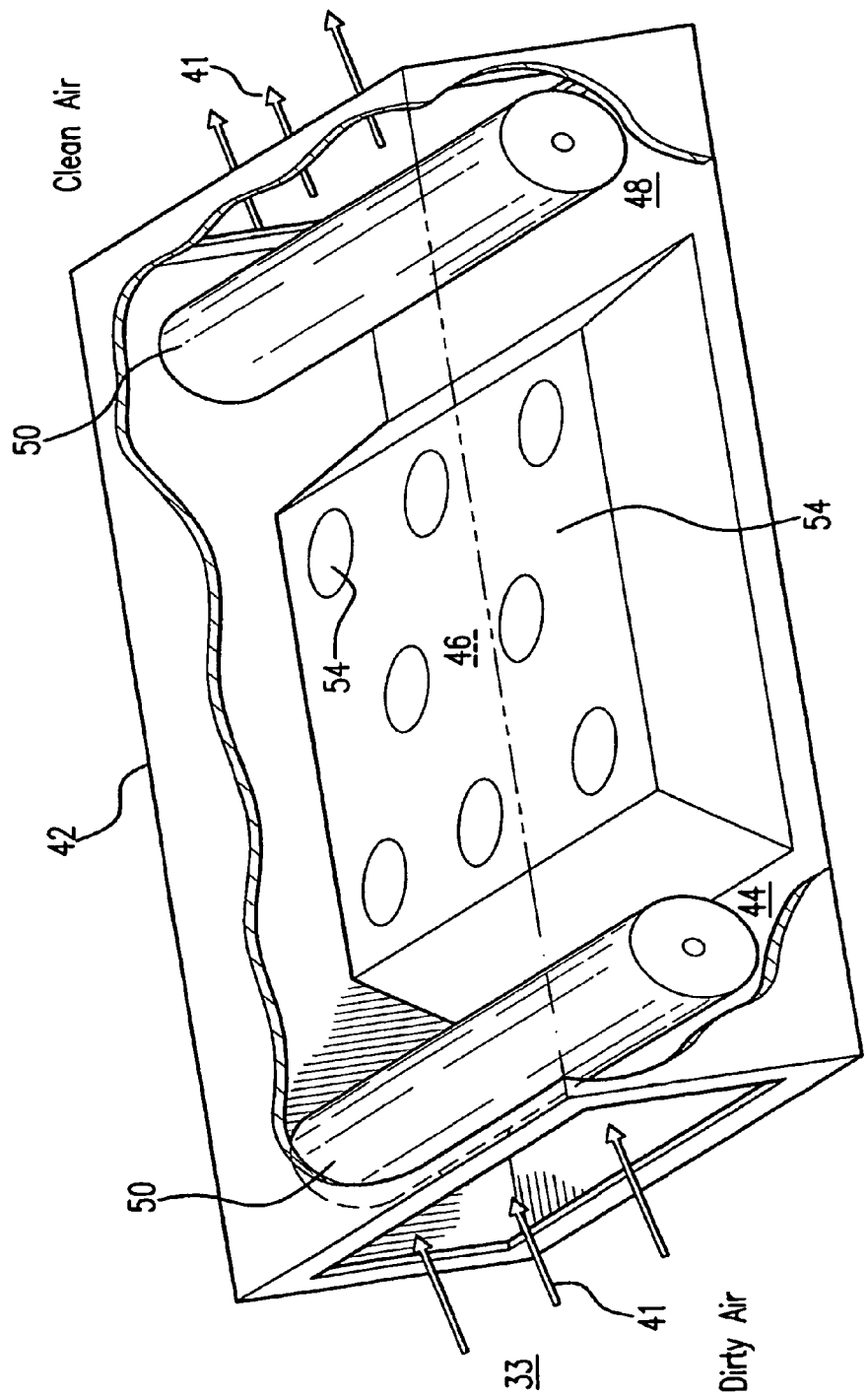
FIG. 11 is a schematic perspective view of an air cleaner unit, according to one embodiment of this invention.
Figure 12:
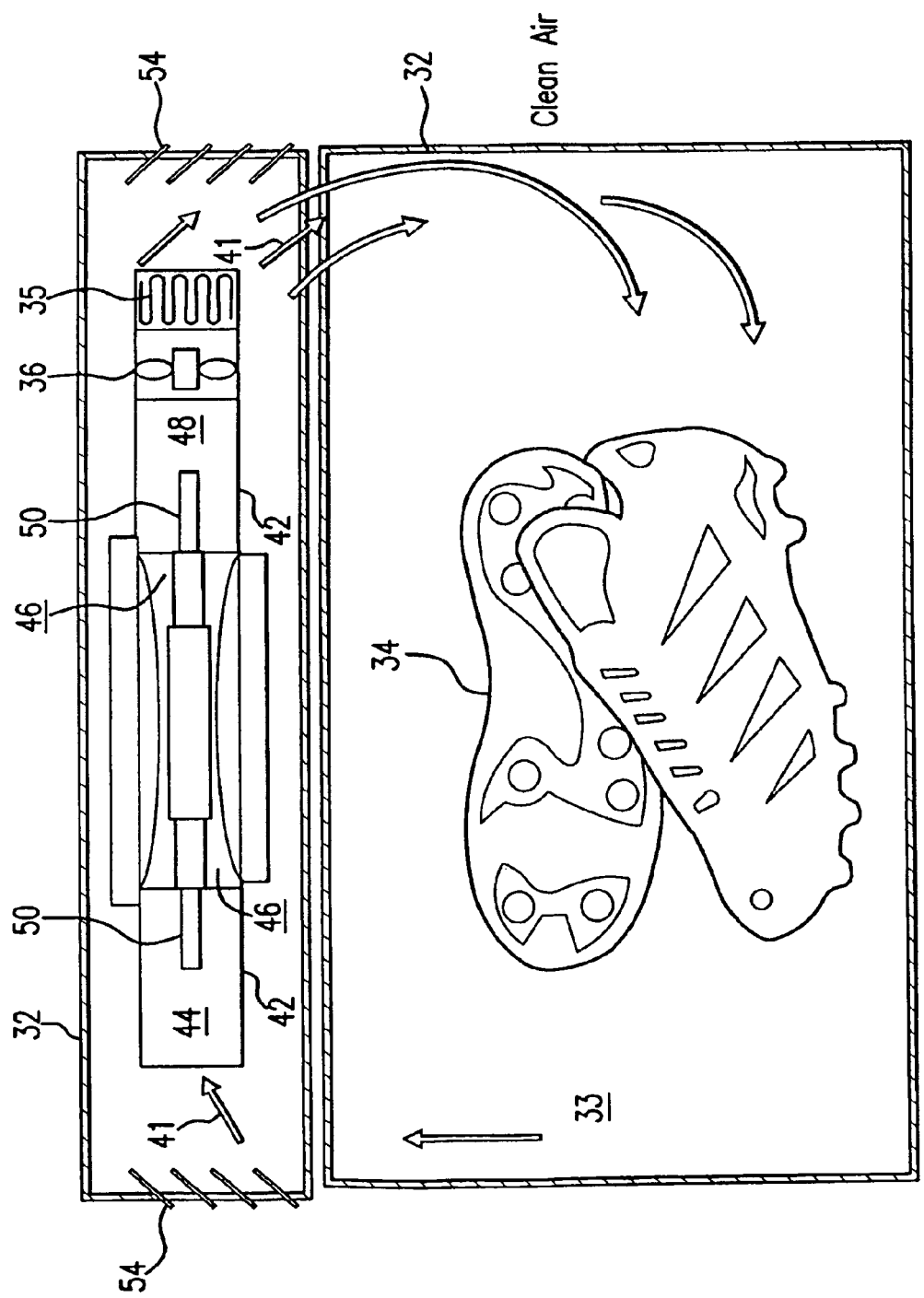
FIG. 12 is a schematic sectional view showing an air cleaner mounted to a housing, according to one embodiment of this invention.

FIG. 1 shows air cleaning unit 40, according to one embodiment of this invention. FIG. 2 shows air cleaning unit 40 positioned or mounted within container 32, such as a truck trailer, according to one embodiment of this invention. FIG. 3 shows air cleaning unit 40 positioned or mounted within a different container 32, according to another embodiment of this invention.

As shown in FIG. 1, air cleaning unit 40 has structure 42, such as a housing, that forms zone 44, zone 46 and zone 48. As air or another suitable atmosphere passes through air cleaning unit 40, such as shown by the arrows of flow direction 41, in FIG. 1, atmosphere 33 passes first through zone 44, then through zone 46, and then through zone 48.

In certain embodiments according to this invention, ozone is generated within atmosphere 33 passing through zone 44. The generated ozone is mixed with atmosphere 33, through zone 46. At least a portion of the generated ozone is removed from the mixed atmosphere, within zone 48. Thus, as the atmosphere discharges from zone 48, the atmosphere has been exposed to generated ozone, mixed with the generated ozone and then disassociated from at least a portion of the generated ozone.

FIGS. 4-7 each shows a different embodiment of air cleaning unit 40, according to this invention. As shown in FIGS. 4-7, UV source 50 comprises a light bulb with an ultraviolet output and/or a corona discharge device that generates ozone within zone 44. Any other suitable mechanical, electro-mechanical and/or other device can be used to generate ozone within zone 44.

FIGS. 1 and 2 show zone 48 downstream with respect to zone 46, and zone 46 downstream with respect to zone 44. In other embodiments according to this invention, zone 46 which is the mixing zone can be at least partially within or part of zone 44 where ozone is generated. In other embodiments according to this invention, zone 48 in which ozone is removed can be at least partially within or part of zone 46, in which mixing occurs. In other embodiments according to this invention, mixing, such as in zone 46, can occur entirely throughout zones 44 and/or 48.

FIG. 1 shows flow diverter 54 positioned within zone 46. In other embodiments according to this invention, flow diverter 54 can be mounted within or exposed to zone 44 and/or zone 48. Flow diverter 54 can be any suitable device that mixes fluid flowing through air cleaning unit 40, including but not limited to a flow nozzle, a baffle, a structure, a mechanical mixer and/or a nozzle, such as a nozzle forming a plurality of flow channels.

As shown in FIGS. 1 and 4-7, for example, mixing can occur by forming a nozzle that has a variable diameter along a flow direction of the atmosphere flowing through air cleaning unit 40. Any suitable venturri nozzle or other converging and/or diverging nozzle can be used to mix the fluid flow.

Figure 19:
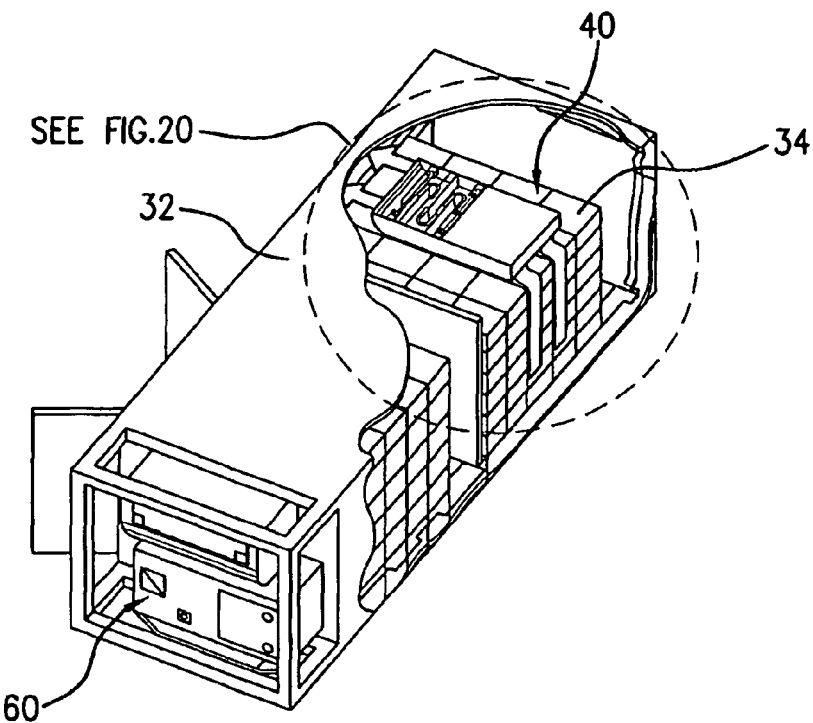
FIG. 19 is a partial cut-away perspective view of an air cleaning unit mounted within a container, according to one embodiment of this invention.
Figure 20:
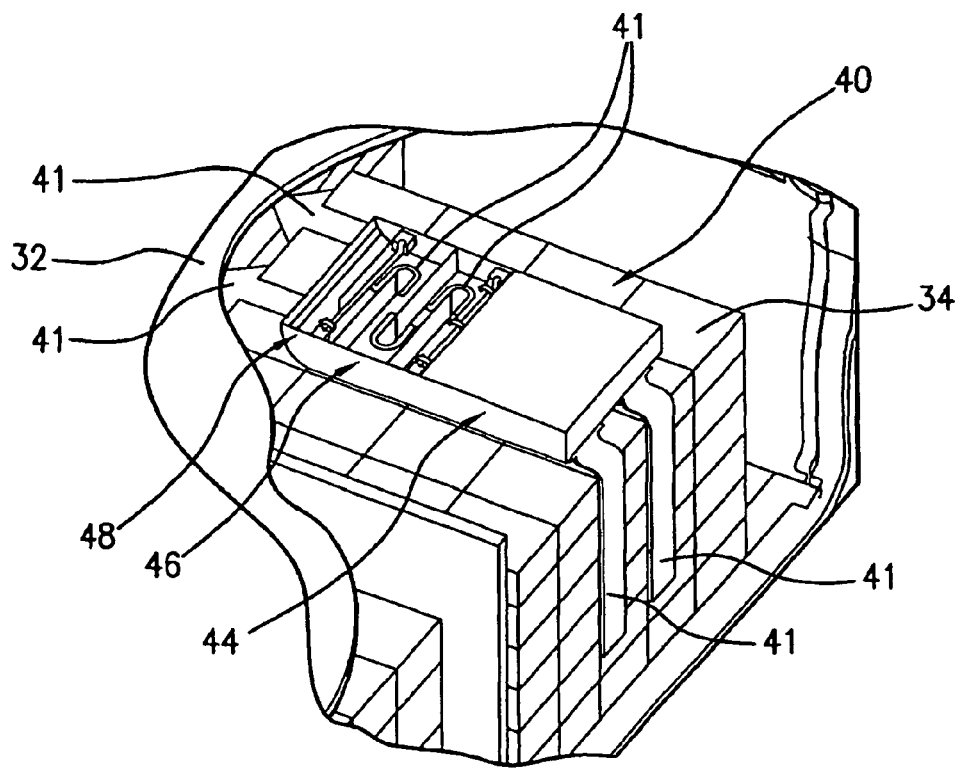
FIG. 20 is an enlarged perspective view showing a partial cut-away section of an air handling unit, according to the embodiment as shown in FIG. 19.

FIGS. 19 and 20 show another embodiment for mixing fluid flowing through air cleaning unit 40. The arrows in FIG. 20 show flow direction 41 along which fluid passes through zone 44, zone 46 and zone 48 of air cleaning unit 40. FIG. 20 shows one particular baffle arrangement. However, any other suitable baffle configuration and design can be used to mix the fluid flow.

FIGS. 19 and 20 show one embodiment of air cleaning unit 40 positioned within container 32 which stores or houses material 34. FIGS. 21-23 show another embodiment of air cleaning unit 40 according to this invention. FIG. 21 shows air cleaning unit 40 mounted within container 32.

FIG. 22 shows structure 42 formed by tubular structural members, for example. Any suitable blower or air moving unit, such as an axial fan and/or a centrifugal blower, can be used to draw fluid into an inlet and discharge fluid through an outlet, for example in flow direction 41 as shown in FIG. 22. Structure 42 as shown in FIGS. 22 and 23 may or may not include flow diverter 54, depending upon the particular intended use and requirements for operation.

FIG. 23 shows UV source 50, for example shown as a light bulb in FIG. 23, that can be used to remove ozone within zone 48. Zone 48 can be positioned as shown in FIG. 22 or in any other suitable position for accomplishing ozone removal or reduction.

Air cleaning unit 40 can be constructed with structure 42 as described in this specification and/or with any other suitable structure that can house or form any zone or chamber used to accomplish ozone generation, mixing and/or ozone removal.

As shown in FIGS. 19-23, structure 42 can be or form an independent apparatus or system that can be positioned within container 32 and/or exposed to atmosphere 33. With an independent arrangement or a stand-alone arrangement of air cleaning unit 40, it is possible to operate air cleaning unit 40 independently of any existing air conditioner 35. For example, an independent system can accommodate flow rates passing through air cleaning unit 40 which are different than flow rates passing through air conditioner 35, such as an existing refrigeration unit mounted within a transport trailer or other container.

Any suitable conventional device for removing ozone can be mounted within or exposed to zone 48. In certain embodiments according to this invention, ozone can be removed or disassociated from zone 48 with a thermal decomposer, a combustible support, a catalytic decomposer, a photo-disassociating device and/or an ultraviolet light source.

In certain embodiments according to this invention, the UV light is generated at a wavelength of about 187 nm to absorb oxygen and thus produce ozone, such as within zone 44. In certain embodiments according to this invention, the UV light is generated at a wavelength of about 254 nm to absorb the ozone and cause photolysis or photo-disassociation. FIG. 18 shows a graph of reducing ozone with ultraviolet light at about 254 nm.

As shown in FIGS. 2 and 3, for example, an outlet of structure 42 which forms air cleaning unit 40 is in communication with zone 48 and atmosphere 33 or the space of container 32. As shown in FIGS. 2 and 3, material 34 is mounted, positioned or otherwise housed within container 32 so that material 34 is exposed to atmosphere 33.

Also shown in FIGS. 2 and 3, air mover 36 can be used to circulate atmosphere 33. Any suitable fan or other air moving device can be used to create flow of atmosphere 33 through air cleaning unit 40. As shown in FIG. 2, air conditioner 35, such as an evaporator or any other suitable air conditioning device, is mounted within atmosphere 33 of container 32.

Container 32 can comprise any suitable structure that defines a chamber or other suitable space for accommodating material 34. Container 32 can be formed by a transportation trailer, a storage trailer, a storage bin, a bag, a shipping container, an equipment bin and/or an expandable structure.

In certain embodiments according to this invention, the method for sanitizing, decontaminating, deodorizing, conditioning, drying or otherwise treating atmosphere 33 begins with generating ozone within atmosphere 33 passing through zone 44. Within zone 46, the generated ozone is mixed with the atmosphere 33 to enhance removal of undesirable contaminates or other elements of atmosphere 33. At least a portion and possibly the entire amount of generated ozone is removed from the mixed atmosphere 33 as it passes through zone 48.

It is possible to mix atmosphere 33 with the generated ozone within zone 44 and/or zone 46. It is possible to continue to mix atmosphere 33 with the generated ozone as it passes through zone 48.

The apparatus of this invention can comprise a control unit, for example located at the exit of the evaporator. The control unit can comprise three sections, including a UV-light (187 nm) ozone generation chamber for generating a relatively high ozone concentration, a mixing zone for removing ethylene with ozone, and a UV-light (254 nm) ozone dissociation chamber for destroying ozone to a level desired for the atmosphere in the container.

The apparatus and/or the method of this invention can comprise a controller or other suitable control system for managing or controlling ozone generation, mixing and/or ozone removal.

In some embodiments of this invention, a controller, such as control 60 as shown in FIG. 19, can communicate or transmit signals through a wired and/or a wireless connection to control any operating parameter and/or function of air cleaning unit 40. In some embodiments of this invention, control parameters are based on timing functions of one or more UV sources 50. It is possible to control the apparatus and/or the method to achieve desired results without requiring, for example, a relatively expensive ethylene sensor and/or a feedback loop. Any control based on timing functions of UV source 50, according to this invention, can be relatively inexpensive and will require reduced maintenance and reduced replacement parts, particularly as compared to a sensor-based control system.

In certain embodiments of this invention, the controller can comprise a transport and storage mode and/or a cleaning mode. In the transport and storage mode, air cleaning unit 40 can cycle with an evaporator. When an evaporate air handler operates, two sets of UV sources 50 can be energized to remove any residual ethylene from atmosphere 33. An override mode can start air mover 36 or any other suitable air handler, for example to begin moving air through the evaporator and/or air cleaning unit 40, for a defined or chosen time period. The controller can then trigger the air handler to start and begin passing fluid through air cleaning unit 40, even if a thermostat or other sensor does not request or call for the evaporator to start.

In certain embodiments of this invention, during the cleaning mode, container 32 can be closed, with or without a lock and/or an alarm, during a cleaning cycle. During the cleaning cycle, UV source 50 or another suitable ozone generator can be energized while fluid passes through air cleaning unit 40, such as for any preset and/or calculated time period. After a defined or calculated time period for generating ozone is reached, UV source 50 can be stopped or not operated while air is circulated through air cleaning unit 40, for example for a time that is sufficient to expose atmosphere 33 and thus kill or remove molds, fungus, spores and/or any other undesired contaminate. Any necessary time period can be calculated from a program of the controller and/or from known data. After the defined and/or calculated time period, UV source 50 can be started within zone 48 to remove ozone from the fluid flowing through air cleaning unit 40.

After the cleaning cycle time period expires, the controller can signal and/or activate to open any lock and/or to deactivate any alarm. The controller can also be used to communicate with and learn information from any suitable sensor that detects a desired parameter or when the ozone concentration is at a certain level, such as when the ozone concentration falls below a level defined by any government agency and/or other guideline recommendation.

The units of this invention can have a low pressure drop and may use a conventional or existing air handler and/or refrigeration system. The ducting and unit structure can be fabricated from plastics, such as PVC, CPVC or from sheet metal with a suitable coating, such as a PTFE coating. The volume of the apparatus can be designed as a function of a size of an evaporator outlet, such as if ducting needs to interface with the refrigeration unit. In certain embodiments, the total volume of the ECU and the ducting connecting it to the evaporator outlet can be approximately 3-5 cubic feet. The UV bulb life can be about 10,000 hours. It is possible that no other part require maintenance in the apparatus, according to certain embodiments of this invention.

It is possible to estimate the required ozone generation capacity of the ozone generation chamber. The required ozone generation rate can be a function of an expected ethylene generation rate. The stoichiometric requirement for oxidation of ethylene by ozone is four moles of ozone for each mole of ethylene destroyed, assuming that only the oxygen radical participates in the oxidation of the hydrocarbon.

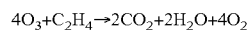

$$4O_3 + C_2H_4 \rightarrow 2CO_2 + 2H_2O + 4O_2$$

Thus, with an ethylene generation scenario having an estimated production of 1 liter per day of ethylene gas in a 20' shipping container, there is a need of 4 liters per day of ozone generation to destroy the ethylene. This volumetric production rate of ozone corresponds to about 0.3 grams per hour of ozone production. Using a design factor of about 10, assuming that only 10% of the UV light emitted by a lamp is absorbed by oxygen, with the remainder absorbed by walls of the duct work, there can be an upper limit on size, power and cost estimates. The performance of commercially available ozone-generating UV lamps is shown in the table of FIG. 15. A U-shaped lamp, 14" long that draws 32 Watts of power can generate the desired level of ozone, such as 3.0 grams per hour.

Instead of estimating an absorption of 10%, an efficiency of UV radiation utilization is calculated using the Beer-Lambert law for attenuation of light traveling through an absorbing medium.

$$\mathrm{Log}(I/Io) = -(a)(p)(l)$$

Where
Io=intensity of light entering the layer of air
I=intensity of light leaving the layer of air
a=absorption coefficient=(0.1)
p=partial pressure of oxygen in air (0.2)
l=absorption path length According to the Handbook of Ozone Technology and Applications (Rice 1984), for oxygen and UV light at a wavelength of 187 nm, "a" is approximately $0.1$ $\mathrm{atm}^{-1}$ $\mathrm{cm}^{-1}$. The partial pressure of oxygen in air is 0.21. With a duct diameter of about 30 centimeters (approximately 1 foot), the absorption of the UV light I/Io will be 0.73, and an expected absorption of the UV light is 27%. Thus, an assumption of 10% is a conservative design approach.

The required volume of the ozone generation chamber can be relatively small, for example approximately 1.2 cubic feet, given a duct diameter of 1 foot and a duct length of about 1.5 feet, to accommodate the UV lamp and associated mounting hardware and a ballast.

The geometry of the mixing chamber can be determined as a function of the actual use or the proposed program. The mixing chamber can have a simple design, such as a continuation of the duct from the ozone generation chamber with at least some change in duct diameter, in order to enhance mixing. A simple, low pressure drop mixing chamber configuration is shown in FIG. 1.

In an ultraviolet (UV) light system, there are two spectral lines that are pertinent to ozone formation. UV light at a wavelength of 187 nm is absorbed by oxygen and causes ozone production. UV light at a wavelength of 254 nm is absorbed by ozone and causes photolysis or photo-dissociation of the ozone. An equivalent lamp to the one selected above, with a glass tube designed to emit at a 254 nm wavelength, will break ozone down to oxygen with an efficiency such as shown in the graph of FIG. 18.

At least some, most or all of the ozone can be removed in the later or downstream chamber of the ECU. For a variety of reasons, it may be desirable to maintain a low level of ozone in the ambient air of the container, for example to have an opportunity to diffuse the ozone into the produce cartons and to oxidize the ethylene in situ. The ozone removal chamber can be sized to achieve the desired exit concentration of ozone. The size and thus residence time of the ozone removal chamber can be estimated by calculating or measuring a UV lamp intensity throughout a duct, and setting the desired ozone concentration at the end of the duct. The resultant residence time sets the required duct length for the desired degree of ozone reduction.

The geometry of the ozone removal chamber can set the ozone removal properties of the system. It is possible to also use an operating sequence. For example, UV lamps can be set to sequence on so that the ozone removal lamp stays on longer than the ozone generating lamp, the chamber size remains small, and the air continues to cycle through the ethylene removal unit after the ozone generation lamps are turned off.

According to this invention, a test facility to conduct ozone generation, ethylene removal and ozone destruction testing can include the following components: instrumentation, including a Thermo Fisher 49i ozone analyzer, a storage control systems electro-chemical ethylene analyzer, voltage and/or current meters to monitor a power draw of lamps or UV source 50; an ozone generator, including a UV lamp G24T6VH/U ozone generator (180 nm wavelength, 25 Watts, 2.3 grams/hour output); an ozone remover, including a UV lamp G24T6/U germicidal lamp (254 nm wavelength, 25 Watts, 8.5 Watts UV output); and a stainless steel model container and flow system, including a container sized at 1/8 scale, flow rates scaled to achieve up to 1 air change per minute, an axial fan positioned in a duct to move air through zones 44, 46 and 48, and high vacuum stainless steel weld fittings to provide leak-free operation.

While in the foregoing detailed description this invention has been described in relation to certain preferred embodiments thereof, and many details have been set forth for purposes of illustration, it will be apparent to those skilled in the art that this invention is susceptible to additional embodiments and that certain of the details described herein can be varied considerably without departing from the basic principles of this invention.

What is claimed is:

1. An apparatus for at least one of sanitizing, decontaminating, deodorizing, conditioning and drying a contaminated atmosphere exposed to a material within a container, the apparatus comprising:
a cleaning unit positioned within the container, an air mover mounted with respect to the cleaning unit and circulating the contaminated atmosphere within the container through the cleaning unit and creating a circulated atmosphere within the cleaning unit, a structure of the cleaning unit forming a first zone, within the first zone an ozone generator generating an ozone within the circulated atmosphere, the structure forming a second zone in which the generated ozone is mixed with the circulated atmosphere, the structure forming a third zone, within the third zone an ozone remover removing at least a portion of the generated ozone from the mixed circulated atmosphere within the cleaning unit, and an outlet of the cleaning unit forming communication between the third zone and the contaminated atmosphere within the container.

2. The apparatus according to claim 1, wherein the ozone generator is an ultraviolet light source within the first zone.

3. The apparatus according to claim 1, wherein with respect to a flow direction of the circulated atmosphere through the structure of the cleaning unit, the second zone is at least one of within the first zone and downstream of the first zone.

4. The apparatus according to claim 1, wherein with respect to a flow direction of the circulated atmosphere through the structure of the cleaning unit, the second zone is at least one of within the third zone and upstream of the third zone.

5. The apparatus according to claim 1, wherein a second structure is mounted within and exposed to the second zone, and the second structure mixes the generated ozone with the circulated atmosphere as the circulated atmosphere passes the second structure.

6. The apparatus according to claim 1, wherein at least one of a thermal decomposer, a combustible support, a catalytic decomposer, a photo-disassociating device and an ultraviolet light source is at least one of mounted within and exposed to the third zone.

7. The apparatus according to claim 1, wherein the outlet of the structure of the cleaning unit forms communication between the third zone and a space of the container.

8. The apparatus according to claim 1, wherein the container is one of a transportation trailer, a storage trailer, a storage bin, a bag, a shipping container, an equipment bin and an expandable structure.

9. The apparatus according to claim 1, further comprising a controller operating at least one parameter corresponding to at least one of the generated ozone, the mixing and the removed ozone.

10. The apparatus according to claim 1, wherein the ozone generator comprises an ultraviolet light source generating ultraviolet light at about 187 nm within the first zone, and the ozone remover comprises an other ultraviolet light source generating ultraviolet light at about 254 nm within the third zone.

11. The apparatus according to claim 1, wherein the generated ozone removes contaminants from the circulated atmosphere within the cleaning unit.

12. The apparatus according to claim 1, wherein the contaminants comprise one of ethylene, an odor, a bacteria, a spore, a microorganism, and a volatile matter.

13. The apparatus according to claim 1, further comprising a controller operating in a cleaning mode, an ozone concentration sensor positioned within the contaminated atmosphere within the container and in communication with the controller, and the controller operating the ozone generator and the ozone remover to achieve a desired ozone concentration in the contaminated air within the container.

* * * * *